(12) United States Patent
Waggoner et al.

(10) Patent No.: US 12,139,758 B2
(45) Date of Patent: Nov. 12, 2024

(54) SURFACE STABILIZATION OF BIOSENSORS

(71) Applicant: LIFE TECHNOLOGIES CORPORATION, Carlsbad, CA (US)

(72) Inventors: Philip Waggoner, Guilford, CT (US); James A. Ball, Ledyard, CT (US); Michael L. Minto, Madison, CT (US); David M. Cox, Foster City, CA (US); Wolfgang Hinz, Killingworth, CT (US); Alexander Mastroianni, Alameda, CA (US); Jeremy Gray, Larkspur, CA (US); Marc Glazer, San Jose, CA (US); Scott Parker, Madison, CT (US); Kimberly Gorrell, Belmont, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 18/407,234

(22) Filed: Jan. 8, 2024

(65) Prior Publication Data

US 2024/0309443 A1    Sep. 19, 2024

Related U.S. Application Data

(60) Continuation of application No. 17/818,869, filed on Aug. 10, 2022, now Pat. No. 11,879,156, which is a
(Continued)

(51) Int. Cl.
*C12Q 1/6869* (2018.01)
*G01N 27/414* (2006.01)

(52) U.S. Cl.
CPC ....... *C12Q 1/6869* (2013.01); *G01N 27/4145* (2013.01)

(58) Field of Classification Search
CPC ................. C12Q 1/6869; G01N 21/75; G01N 2021/752; G01N 2021/757; B01L 3/5027; B01L 3/502715
See application file for complete search history.

(56) References Cited

U.S. PATENT DOCUMENTS 3,281,606 A   10/1966   Lueck
3,943,557 A   3/1976   Frazee et al.
(Continued)

FOREIGN PATENT DOCUMENTS

CN   102203282 A   9/2011
CN   103370425 A   10/2013
(Continued)

OTHER PUBLICATIONS

Clausen et al., "Chromatographic Characterization of Phosphonate Analog EDTA-Modified Zirconia Support for Biochromatographic Applications", Analytical Chemistry, vol. 70, No. 2, Jan. 15, 1998, pp. 378-385.
(Continued)

*Primary Examiner* — Brian J. Sines

(57) ABSTRACT

A sensor apparatus includes a substrate, a semiconductor device disposed over the substrate, the semiconductor device having a surface electrode structure, and a saccharide coating formed over the surface electrode structure. The saccharide coating can be removed prior to use. The semiconductor device can further include a well and optionally a bead disposed in the well.

1 Claim, 17 Drawing Sheets

Related U.S. Application Data division of application No. 16/824,920, filed on Mar. 20, 2020, now Pat. No. 11,441,178, which is a division of application No. 16/182,384, filed on Nov. 6, 2018, now Pat. No. 10,619,201, which is a division of application No. 15/061,273, filed on Mar. 4, 2016, now Pat. No. 10,724,086.

(60) Provisional application No. 62/128,916, filed on Mar. 5, 2015.

(56) References Cited

U.S. PATENT DOCUMENTS

| | | | |
|---|---|---|---|
| 4,070,203 | A | 1/1978 | Neisius et al. |
| 4,153,627 | A | 5/1979 | Delbende et al. |
| 4,165,295 | A | 8/1979 | Vander Mey |
| 4,395,348 | A | 7/1983 | Lee |
| 4,425,384 | A | 1/1984 | Brownscombe |
| 4,480,005 | A | 10/1984 | Brownscombe |
| 4,491,530 | A | 1/1985 | Thomas |
| 4,522,977 | A | 6/1985 | Gardner |
| 4,522,978 | A | 6/1985 | Gardner |
| 4,532,296 | A | 7/1985 | Gardner |
| 4,532,297 | A | 7/1985 | Gardner |
| 4,599,401 | A | 7/1986 | Koleske |
| 4,618,458 | A | 10/1986 | Prillieux et al. |
| 4,626,570 | A | 12/1986 | Gardner |
| 4,629,779 | A | 12/1986 | Koleske |
| 5,344,967 | A | 9/1994 | Schnur et al. |
| 6,071,392 | A | 6/2000 | Yamamoto et al. |
| 6,087,529 | A | 7/2000 | Mathieu et al. |
| 6,140,144 | A | 10/2000 | Najafi et al. |
| 6,300,141 | B1 | 10/2001 | Segal et al. |
| 6,479,019 | B1 | 11/2002 | Goldstein et al. |
| 9,685,689 | B1 | 6/2017 | Etzkorn et al. |
| 10,619,201 | B2 | 4/2020 | Waggoner et al. |
| 10,724,086 | B2 | 7/2020 | Waggoner et al. |
| 11,441,178 | B2 | 9/2022 | Waggoner et al. |
| 11,879,156 | B2 * | 1/2024 | Waggoner .......... G01N 27/4145 |
| 2002/0068685 | A1 | 6/2002 | Wojtczak et al. |
| 2006/0102471 | A1 | 5/2006 | Maurer et al. |
| 2009/0127589 | A1 | 5/2009 | Rothberg et al. |
| 2010/0301398 | A1 | 12/2010 | Rothberg et al. |
| 2013/0084500 | A1 | 4/2013 | Takimoto et al. |
| 2013/0189790 | A1 | 7/2013 | Li et al. |
| 2013/0225421 | A1 | 8/2013 | Li et al. |
| 2013/0240375 | A1 | 9/2013 | Blythe et al. |
| 2013/0324421 | A1 | 12/2013 | Rothberg et al. |
| 2014/0191292 | A1 | 7/2014 | Inman et al. |
| 2016/0061773 | A1 | 3/2016 | Ball et al. |
| 2016/0258011 | A1 | 9/2016 | Waggoner et al. |

FOREIGN PATENT DOCUMENTS

| | | |
|---|---|---|
| CN | 103901090 A | 7/2014 |
| WO | WO-2003046540 A1 | 6/2003 |
| WO | WO-2004083843 A1 | 9/2004 |
| WO | WO-2014013263 A1 | 1/2014 |
| WO | WO-2014160962 A2 | 10/2014 |

OTHER PUBLICATIONS

EP Extended Search Report dated Dec. 8, 2020, to EP Patent Application No. 20195062.3.

EP18213839.6, Search Report, Feb. 19, 2019, 8 pages.

First Office action issued on Jul. 17, 2020, to CN Patent Application No. 201680013987.8.

Hu et al., "Synthesis and Characterization of New Zirconia-Based Polymeric Cation-Exchange Stationary Phases for High-Performance Liquid Chromatography of Proteins", Analytical Chemistry, vol. 70, No. 9, 1998, pp. 1934-1942.

Kuo et al., "Field-effect transistor with polyaniline think film as semiconductor", Synthetic Metals, vol. 88, No. 1, Apr. 1997, pp. 23-30.

Nawrocki et al., "Chemistry of Zirconia and its use in Chromatography", Journal of Chromatography A, vol. 657, No. 2, Dec. 1993, pp. 229-282.

Nawrocki et al., "New Materials for Biotechnology: Chromatographic Stationary Phases Based on Zirconia", Biotechnology Progress, vol. 10, No. 6, 1994, pp. 561-573.

Nawrocki et al., "Part 1: Chromatography using ultra-stable metal oxide-based stationary phases for HPLC", Journal of Chromatography A, vol. 1028, No. 1, Feb. 27, 2004, pp. 1-30.

Nawrocki et al., "Part II: Chromatography using ultra-stable metal oxide-based stationary phases for HPLC", Journal of Chromatography A, vol. 1028, No. 1, Feb. 27, 2004, pp. 31-62.

PCT/US2016/020918, Partial Search Report, May 6, 2016, 6 pages.

PCT/US2016/020918, Search Report and Written Opinion, Jul. 14, 2016, 18 pages.

Second Office action issued on Mar. 1, 2021, to CN Patent Application No. 201680013987.8.

* cited by examiner

SURFACE STABILIZATION OF BIOSENSORS

CROSS-REFERENCE TO RELATED APPLICATIONS

This application is a continuation application of U.S. application Ser. No. 17/818,869, filed Aug. 10, 2022. U.S. application Ser. No. 17/818,869 is a divisional application of U.S. application Ser. No. 16/824,920, filed Mar. 20, 2020, now U.S. Pat. No. 11,441,178. U.S. Pat. No. 11,441,178 is a divisional application of U.S. application Ser. No. 16/182,384, filed Nov. 6, 2018, now U.S. Pat. No. 10,619,201. U.S. Pat. No. 10,619,201 is a divisional application of U.S. application Ser. No. 15/061,273, filed Mar. 4, 2016, now U.S. Pat. No. 10,724,086. U.S. Pat. No. 10,724,086 claims benefit of U.S. Application No. 62/128,916, filed Mar. 5, 2015. All applications identified in this section are herein incorporated by reference, each in its entirety.

FIELD OF THE DISCLOSURE

This disclosure, in general, relates to surface stabilized biosensors and methods of stabilizing such biosensors.

BACKGROUND

There is increasing interest in electronic sensors for detecting chemical and biological agents, analytes, or reaction byproducts. Furthermore, there is a push to develop sensors with greater sensitivity, capable of detecting ever smaller changes in concentration or solution pH. There is also a move to decrease reaction volumes, particularly when detecting the byproducts of reactions.

In one exemplary system, pH-based sequencing of biomolecules, such as nucleic acids or proteins, utilizes small changes in pH in reaction volumes on the order of nanoliters or smaller. For example, target nucleic acids can be disposed in volumes of less than a nanoliter and nucleotide incorporation along the target nucleic acids can be detected based on small changes in pH resulting from the nucleotide incorporation.

The reliability of such sensitive sensors can be influenced by both the stability of the sensor devices and the consistency of the sensor calibration. Such stability and consistent calibration can be affected by packaging, storage, and transportation.

SUMMARY

In an exemplary embodiment, a sensor apparatus includes a substrate, a semiconductor device disposed over the substrate, and a flow cell lid. The semiconductor device has a surface electrode structure. A flow cell is defined between the substrate and the flow cell lid. In an example, a saccharide solution can be applied through the flow cell and over the semiconductor device, forming a saccharide coating over the surface electrode structure of the semiconductor device. The sensor apparatus can be dried and package, leaving the saccharide coating over the surface electrode structure during transport and storage. At a point of use, a wash solution can be applied through the flow cell, removing the saccharide coating and exposing the surface electrode structure to fluid passing through the flow cell.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, a sensor apparatus includes a substrate, a semiconductor device disposed over the substrate, and a flow cell lid. The semiconductor device has a surface electrode structure. The semiconductor device can further include a well structure defining wells over the surface electrode structures. Optionally, beads can be disposed in the wells, and the beads can be conjugated to nucleic acids. A flow cell is defined between the substrate and the flow cell lid. In an example, a saccharide solution can be applied through the flow cell and over the semiconductor device, forming a saccharide coating over the surface electrode structure of the semiconductor device and optionally, over a bead. The sensor apparatus can be dried and package, leaving the saccharide coating over the surface electrode structure during transport and storage. At a point of use, a wash solution can be applied through the flow cell, removing the saccharide coating and exposing the surface electrode structure to fluid passing through the flow cell.

Figure 1:
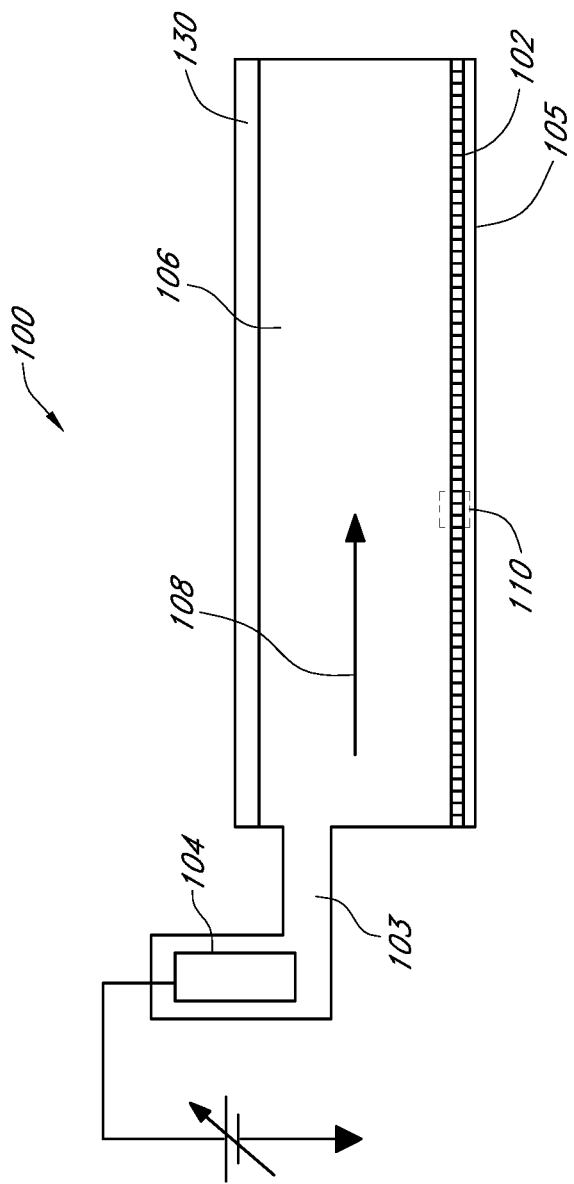
FIG. 1, FIG. 2A, FIG. 2B and FIG. 2C include illustrations of portions of an exemplary sensor apparatus.

In a particular embodiment, a sequencing system uses a sensor apparatus that includes a flow cell to which a sensory array is exposed. The sequencing system includes communication circuitry in electronic communication with the sensory array, and includes containers and fluid controls in fluidic communication with the flow cell. In an example, FIG. 1 illustrates an expanded and cross-sectional view of a flow cell 100 and illustrates a portion of a flow chamber 106. A reagent flow 108 flows across a surface of a microwell array 102, in which the reagent flow 108 flows over the open ends of microwells of the microwell array 102. The microwell array 102 and a sensor array 105 together can form an integrated unit forming a lower wall (or floor) of flow cell 100. A reference electrode 104 can be fluidly coupled to flow chamber 106. Further, a flow cell cover or lid 130 encapsulates flow chamber 106 to contain reagent flow 108 within a confined region.

Figure 2A:
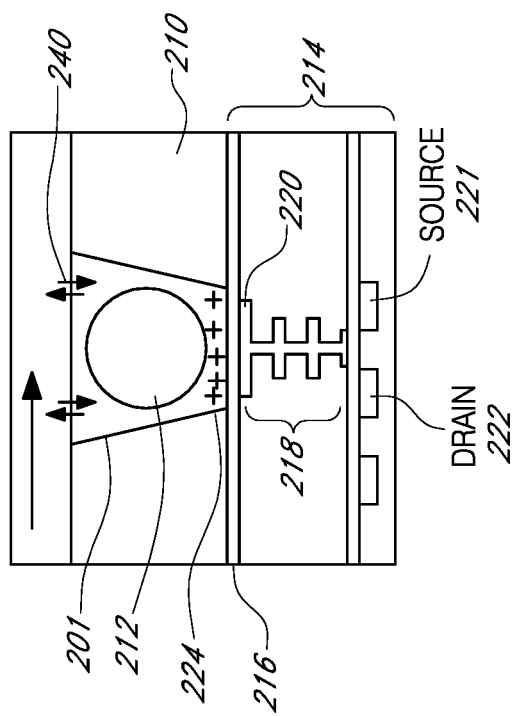

FIG. 2A illustrates an expanded view of a microwell 201 and a sensor 214, as illustrated at 110 of FIG. 1. The volume, shape, aspect ratio (such as base width-to-well depth ratio), and other dimensional characteristics of the microwells can be selected based on the nature of the reaction taking place, as well as the reagents, byproducts, or labeling techniques (if any) that are employed. The sensor 214 can be a chemical field-effect transistor (chemFET), more specifically an ion-sensitive FET (ISFET), with a floating gate 218 having a sensor plate 220 optionally separated from the microwell interior by a passivation layer 216 or other metal, metal nitride, or metal oxide layers, or combinations thereof. Together, the sensor plate 220, optional passivation layer 216, or other layers form an electrode structure. The sensor 214 can be responsive to (and generate an output signal related to) the amount of a charge 224 present on the passivation layer 216 opposite the sensor plate 220. Changes in the charge 224 can cause changes in a current between a source 221 and a drain 222 of the chemFET. In turn, the chemFET can be used directly to provide a current-based output signal or indirectly with additional circuitry to provide a voltage-based output signal. Reactants, wash solutions, and other reagents can move in and out of the microwells by a diffusion mechanism 240.

In an embodiment, reactions carried out in the microwell 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, then multiple copies of the same analyte can be analyzed in the microwell 201 at the same time to increase the output signal generated. In an embodiment, multiple copies of an analyte can be attached to a solid phase support 212, either before or after deposition into the microwell 201. The solid phase support 212 can be microparticles, nanoparticles, beads, solid or porous comprising gels, or the like. For simplicity and ease of explanation, the solid phase support 212 is also referred herein as a bead or particle. For a nucleic acid analyte, multiple, connected copies can be made by rolling circle amplification (RCA), exponential RCA, or like techniques, to produce an amplicon without the use of a solid support.

Figure 2B:
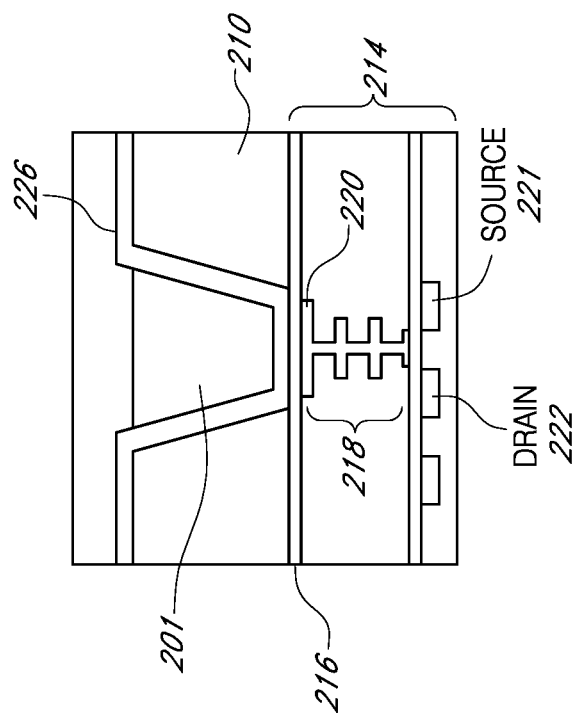

Signal quality from the chemFET can be influenced by surface qualities of the microwell 201 and electrode structure. To protect or stabilize the surface, a saccharide coating can be applied over the surfaces. For example, as illustrated in FIG. 2B, following assembly and prior to use, a saccharide coating 226 can be formed over the sensor structure 214. The saccharide coating 226 can be conformal, as illustrated in FIG. 2B. Alternatively, the saccharide coating can fill the microwell 201 and optionally portions of the flow cell 106.

Figure 2C:
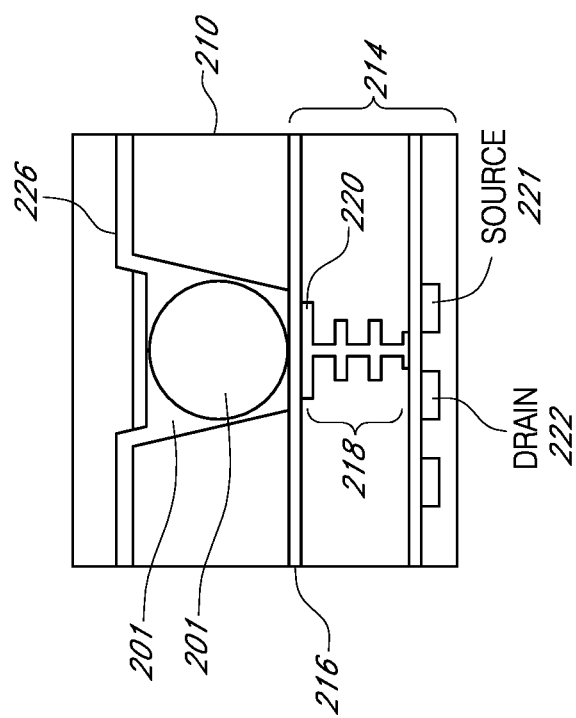

In a further example, a bead can be disposed in the well. For example, as illustrated in FIG. 2C, the saccharide coating 226 can be formed over the bead 212 and over the sensor structure 214. The saccharide coating can be conformal or fill the microwell 201, and can optional occupy portions of the flow cell 106.

Prior to use, a wash solution can be applied through the flow cell 106 to remove the saccharide coating 226, providing a microwell 201 into which, for example, a solid phase support 212 can be provided and measurements of ion concentration or pH can be made, or when a solid support is present prior to washing, the solid support can be exposed for use in measurements.

Figure 3:
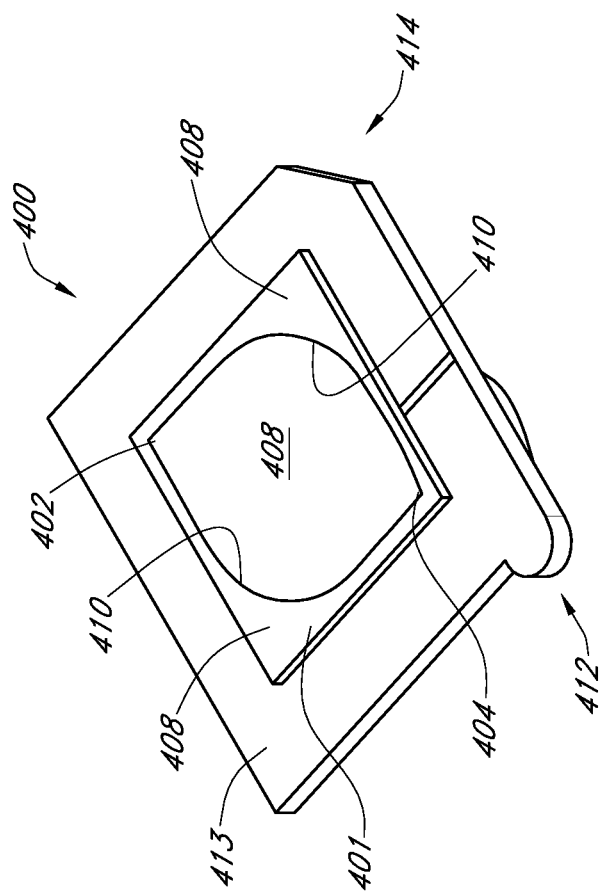
FIG. 3, FIG. 4, FIG. 5, and FIG. 6 include illustrations of exemplary sensor apparatuses.
Figure 4:
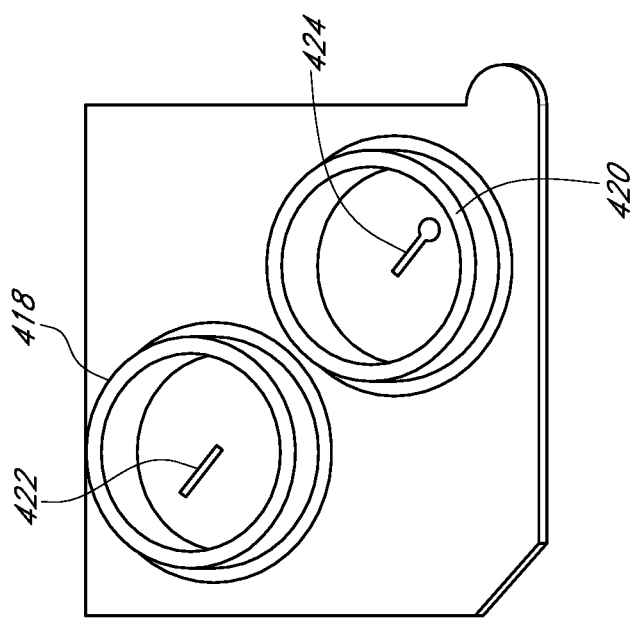
Figure 5:
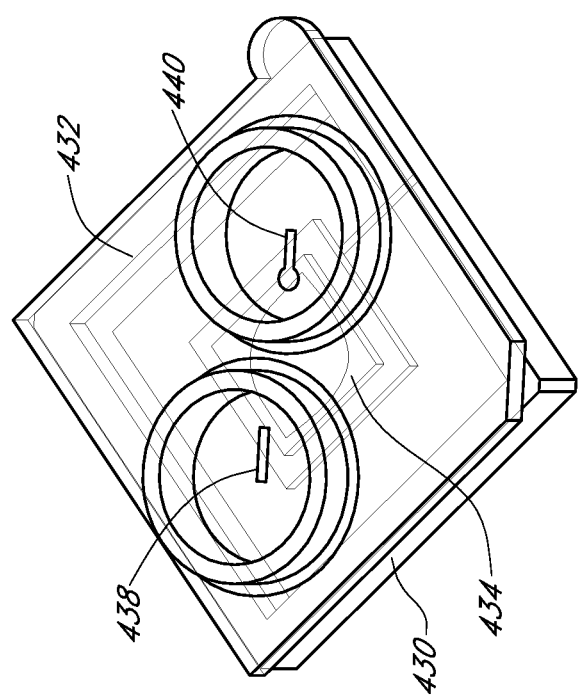
Figure 6:
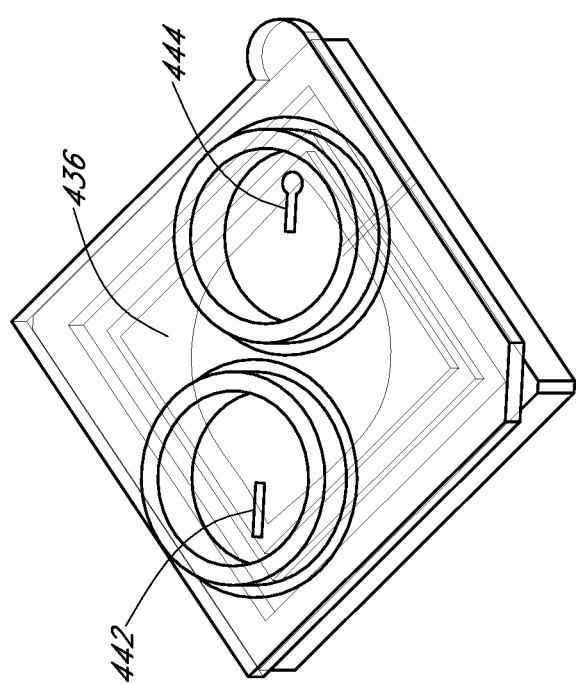

Flow cells can be assembled with a microwell array and sensor array in a variety of ways. In one embodiment, illustrated in FIGS. 3-6, a flow cell is made by attaching a fluidic interface member to a housing containing a sensor chip. Typically, an integrated microwell-sensor array (i.e., a sensor chip) is mounted in a housing or package that protects the chip and provides electrical contacts for communicating with other devices. A fluidics interface member is designed to provide a cavity or flow chamber for reagents to pass through when it is sealingly attached to such packaging. In one aspect, such attachment is accomplished by gluing the pieces together. FIG. 3 illustrates a bottom view (or face) of a component 400 of a flow cell. In the illustrated embodiment, a complete flow cell is formed by attaching the component 400 to a package containing a sensor array (as shown in FIGS. 5 and 6). A ridge 401 is elevated from a surface 413 and forms walls 410 of an ellipsoidal flow chamber 408 when mated with the chip 430 illustrated in FIG. 5. The component 400 can be glued to the chip housing 430 to form a fluid-tight seal. FIG. 4 illustrates a top view (or face) 416 of the component or member 400 showing inlet and outlet collars 418 and 420 that permit the flow cell to be sealingly connected to a fluidic system. Inlet and outlet tubes connected to elastomeric annular members can be inserted into the collars 418 and 420 so that the elastomeric material forms a seal along the floor and walls of collars 418 and 420. Other methods of connecting a flow cell to a fluidics system can be used, including other types of pressure fittings, clamp-based fittings, screw-on fittings, or the like. The component 400 can be adapted to accommodate different sized chips with a simple design change, as illustrated by passages 422 and 424. Namely, for a small array 434 illustrated in FIG. 5, a passage having an opening at the center of the inlet collar 418 and of the outlet collar 420 can be directed by such passage towards the center of the component or member 400 to an inlet port and outlet port over the array 430. Likewise, for a large array 436, illustrated in FIG. 6, similar passages 442 and 444 can be directed away from the center of the component 400 and to the inlet and outlet of the array 436. Such a design advantageously provides a single basic flow cell design that can be used with multiple sensor array sizes. A protruding tab 412 and a bevel 414 can be employed to ensure correctly oriented placement of a chip into a complementary socket or appliance for making fluidic and electrical connections to the rest of the apparatus.

Figure 7:
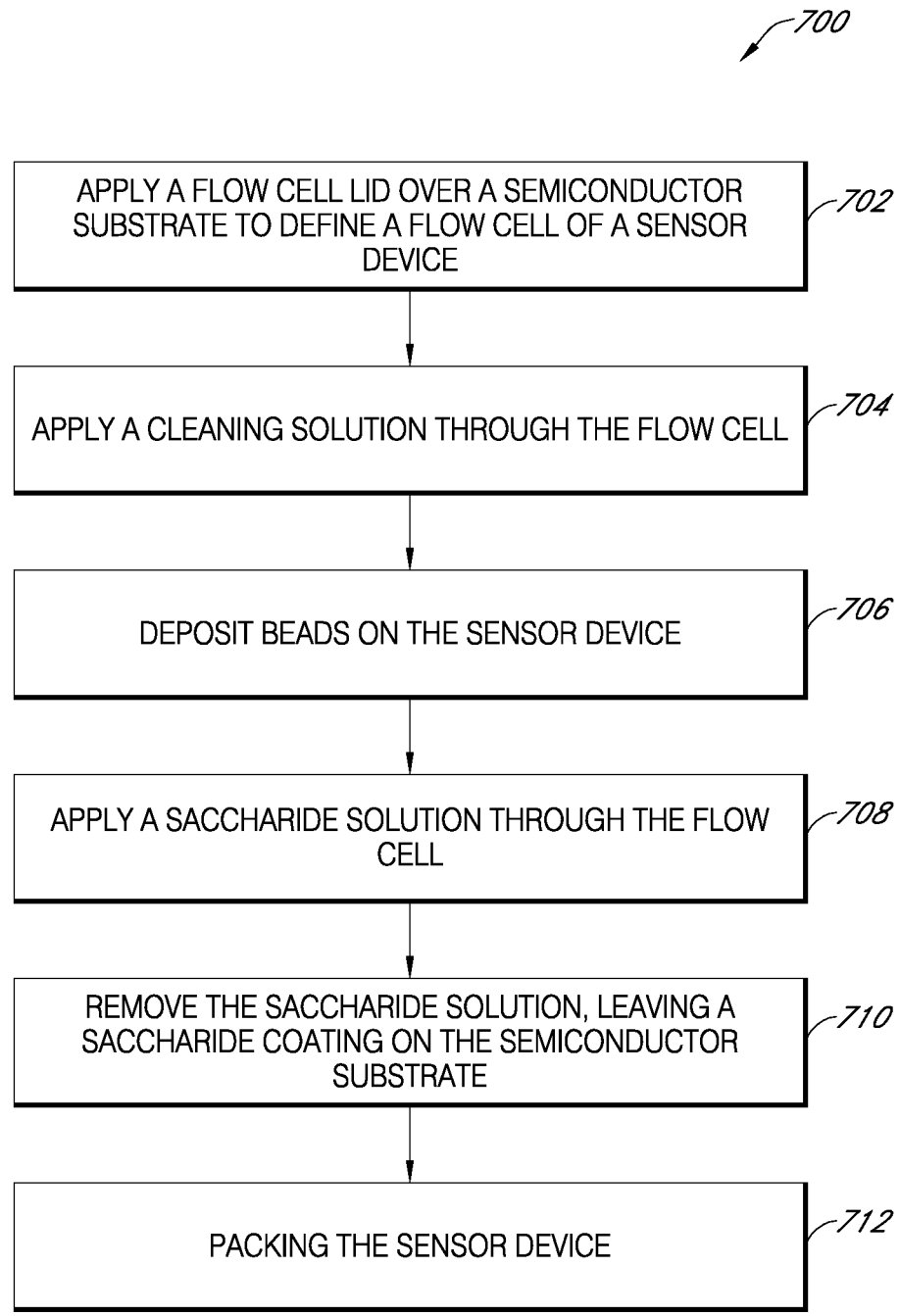
FIG. 7 and FIG. 8 include illustrations of exemplary methods for treating and using a sensor apparatus.

The chip or chip assembly can be treated to protect the sensors or beads disposed on the chip during transportation. In a particular example, as illustrated in FIG. 7, a method 700 includes applying a flow cell lid over a semiconductor substrate to define a flow cell of a sensor apparatus, as illustrated at 702. Access ports through the flow cell lid can provide fluidic access to the flow cell sensor devices of the sensor apparatus. The sensor devices can include electrode or gate structures that are exposed to fluids applied through flow cell lid and flowing through flow cell.

As illustrated at 704, a cleaning solution can be applied through the flow cell. The cleaning solution can be a base solution, such as a solution including NaOH, an acid solution, or a combination thereof. In an example, the acid solution is a non-aqueous solution including an anionic surfactant, such as a sulfonic acid surfactant, for example, dodecyl benzene sulfonic acid (DBSA). In particular, the semiconductor substrate can be cleaned using a sequence of flowing the non-aqueous acid solution, water or alcohol and the base solution.

Optionally, beads can be deposited over the sensor device, for example, in wells formed over the semiconductor substrate, as illustrated at 706. Optionally, the beads can be conjugated to a biomolecule, such as a nucleic acid.

In an example, the beads can be formed from a polymer network, such as a non-nucleic acid polymer network. Exemplary non-nucleic polymer networks agarose; polyethylene glycol; polyoxybutylene; diethylacrylamide; polyoxyethylene; polyacrylamide; polyoxypropylene; N,N-polydimethylacrylamide; poly(N-isopropylacrylamide); polyvinylpyrrolidone; poly-N-hydroxyacrylamide; the like; or any combination thereof. In a particular example, the polymer network includes polyethylene glycol. In another example, the polymer network includes polyacrylamide. In particular, the polymer network can form a hydrogel. For example, the bead when in an aqueous solution can have 0.1% to 10% polymer by weight, such as 0.5% to 8% polymer or 0.8% to 5% polymer.

In a further example, the beads can be conjugated to a biomolecule. In a particular example, the biomolecule can be covalently bonded to the polymer network of the bead either directly or through a linker. The biomolecule can be a nucleic acid, such as DNA or RNA. In particular, the nucleic acid can be an oligonucleotide, such as a capture probe or a primer. In another example, the nucleic acid can be a polynucleotide to be sequenced.

In an example, as illustrated 708, a saccharide solution can be applied through the flow cell. In an example, the saccharide solution is an aqueous solution that includes a saccharide. Optionally, the saccharide solution can also include a surfactant. In a further example, the saccharide solution can include an alcohol.

The saccharide can include a monosaccharide, a disaccharide, a polysaccharide, a derivative thereof, or a combination thereof. In an example, a monosaccharide includes glucose, fructose, galactose, or a combination thereof. In another example, a disaccharide includes sucrose, trehalose, maltose, or lactose, or a combination thereof. In a particular example, the disaccharide includes sucrose. In another example, the disaccharide includes trehalose. In a further example, the saccharide can include hyaluronic acid. The saccharide can be included in the saccharide solution in a range of 5 wt % to 30 wt %, such as a range of 5 wt % to 20 wt %, a range of 10 wt % to 20 wt %, or a range of 10 wt % to 15 wt %.

The saccharide solution can further include a surfactant. The surfactant can be an ionic surfactant, an amphoteric or zwitterionic surfactant, a non-ionic surfactant, or a combination thereof. The ionic surfactant can be an anionic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate (e.g., dodecyl benzene sulfonic acid or salts thereof); or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

In another example, the ionic surfactant can be a cationic surfactant. An exemplary cationic surfactant includes primary, secondary or tertiary amines, quaternary ammonium surfactants, or any combination thereof. An exemplary quaternary ammonium surfactant includes alkyltrimethylammonium salts, such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric or zwitterionic surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl) dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin. In a further example, the amphoteric or zwitterionic surfactant can be an alkylamino alkylsulfonate, such as an alkyl dimethyl ammonio propane sulfonate, where the alkyl group has between 5 and 20 carbons, for example, between 8 and 18 carbons, between 8 and 14 carbons, or between 10 and 14 carbons. In a particular example, the surfactant includes n-dodecyl-N,N-dimethyl-3-ammonio-1-propanesulfonate.

In another example, the surfactant can be a non-ionic surfactant such as a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, or a combination thereof. In a particular example, the polyethylene-glycol-based surfactant includes a polyethylene-glycol ether, such as an alkylphenol polyethoxylate. In a further example, the non-ionic surfactant can be an alkyl polysaccharide. In another example, the non-ionic surfactant includes a non-ionic fluorosurfactant, such as an ethoxylated fluorocarbon. In a further example, the surfactant solution can include octyl pyrrolidine.

In particular, the surfactant solution can include combinations of such surfactants. For example, the surfactant solution can include a combination of a zwitterionic surfactant with an anionic surfactant. In a particular example, the surfactant solution can include a zwitterionic surfactant, such as an alkylamino alkylsulfonate, and an anionic surfactant, such as a sulfate surfactant, for example SDS.

In an example, the surfactant solution can include one or more surfactants having a total concentration in the range of 0.001% to 20% by weight. For example, surfactant can be included in a total amount in a range of 0.01% to 10.0%, such as a range of 0.01% to 5.0%, a range of 0.05% to 1.0%, or a range of 0.05% to 0.5% by weight.

In a further example, the surfactant solution can include an alcohol, such as methanol, ethanol, isopropyl alcohol, isobutyl alcohol, or a combination thereof. In an example, the alcohol can be included in an amount in a range of 5.0 wt % to 70.0 wt %, such as a range of 10 wt % to 50 wt %.

As illustrated at 710, the saccharide solution can be removed from the flow cell, leaving a saccharide coating on the semiconductor substrate. The saccharide coating can be conformal. In another example, the saccharide coating can fill the wells defined over the semiconductor substrate. In particular, the saccharide coating is disposed over electrode structures of sensor devices on the semiconductor substrate.

As illustrated at 712, the sensor apparatus can be packaged. For example, the sensor apparatus can be dried and then inserted into a sealed package for shipping. In an example, the packaging has electrostatic dissipative characteristics. In another example, the packaging can be water or humidity resistant. In an additional example, a desiccant can be added to the packaging. As such, the saccharide coating remains in contact with the sensor device for transport and storage of the sensor apparatus.

Figure 8:
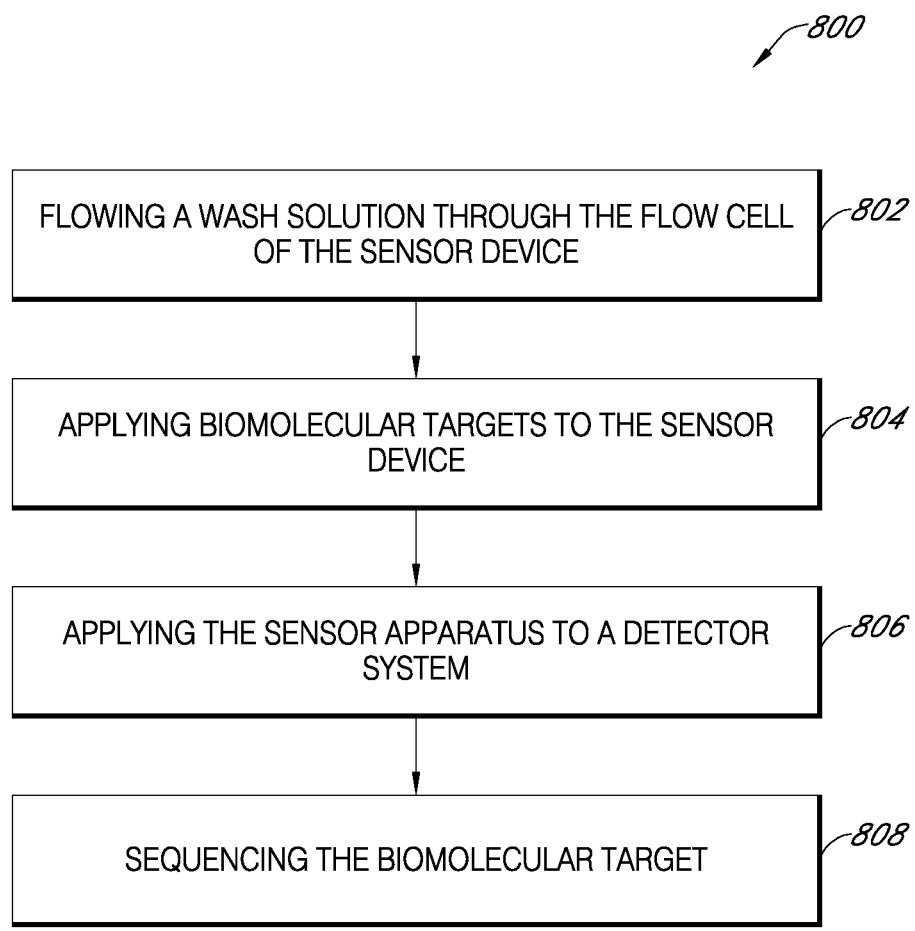

At the point of use, the saccharide coating can be removed in preparation for utilizing the sensor apparatus. As illustrated in FIG. 8, a method 800 includes flowing a wash solution through the flow cell of the sensor apparatus, as illustrated at 802. In an example, the wash solution can be water or an aqueous solution. In a further example, the wash solution can include a surfactant. In an additional example, the wash solution can include an alcohol. An exemplary alcohol includes ethanol, methanol, isopropyl alcohol, isobutyl alcohol, or a combination thereof. In an example, the alcohol can be included in an amount in a range of 5 wt % to 70 wt %, such as a range of 10% to 50%. In another example, pure alcohol can be used.

The wash solution flowing through the flow cell removes the saccharide coating and exposes a sensor electrode structure of the sensor devices and optionally, a bead. Following removal of the saccharide coating, the sensor can be used.

For example, a biomolecular target, such as a nucleic acid or protein, can be applied to the sensor apparatus, as illustrated at 804. In a particular example, nucleic acids or proteins can be applied over a sensor electrode of the sensor device. In an example, the biomolecular target is attached to a bead and deposited in a well of the sensor device. In another example, wells of the sensor device can include beads prior to washing, and the biomolecular target can be captured by such beads. In a particular example, a nucleic acid target can be captured by a bead having a complementary oligonucleotide and optionally amplified to provide a plurality of copies of the nucleic acid target on the bead. In particular, a plurality of copies of nucleic acids can be applied over a sensor device and sequencing-by-synthesis can be performed through the detection of changes in pH in response to nucleotide incorporation.

As illustrated at 806, the sensor apparatus can be applied to a detector system. For example, the sensor apparatus can be connected fluidically to a set of reagents and can be connected electronically to measurement and control systems. A series of reagents can be applied to a flow cell of the sensor apparatus, and measurements can be made using the sensor devices of the sensor apparatus. In a particular example, as illustrated at 808, a biomolecular target can be sequenced using such a detector system. For example, nucleic acids can be sequenced using sequencing-by synthesis and detecting changes in pH using the sensor devices.

Figure 9:
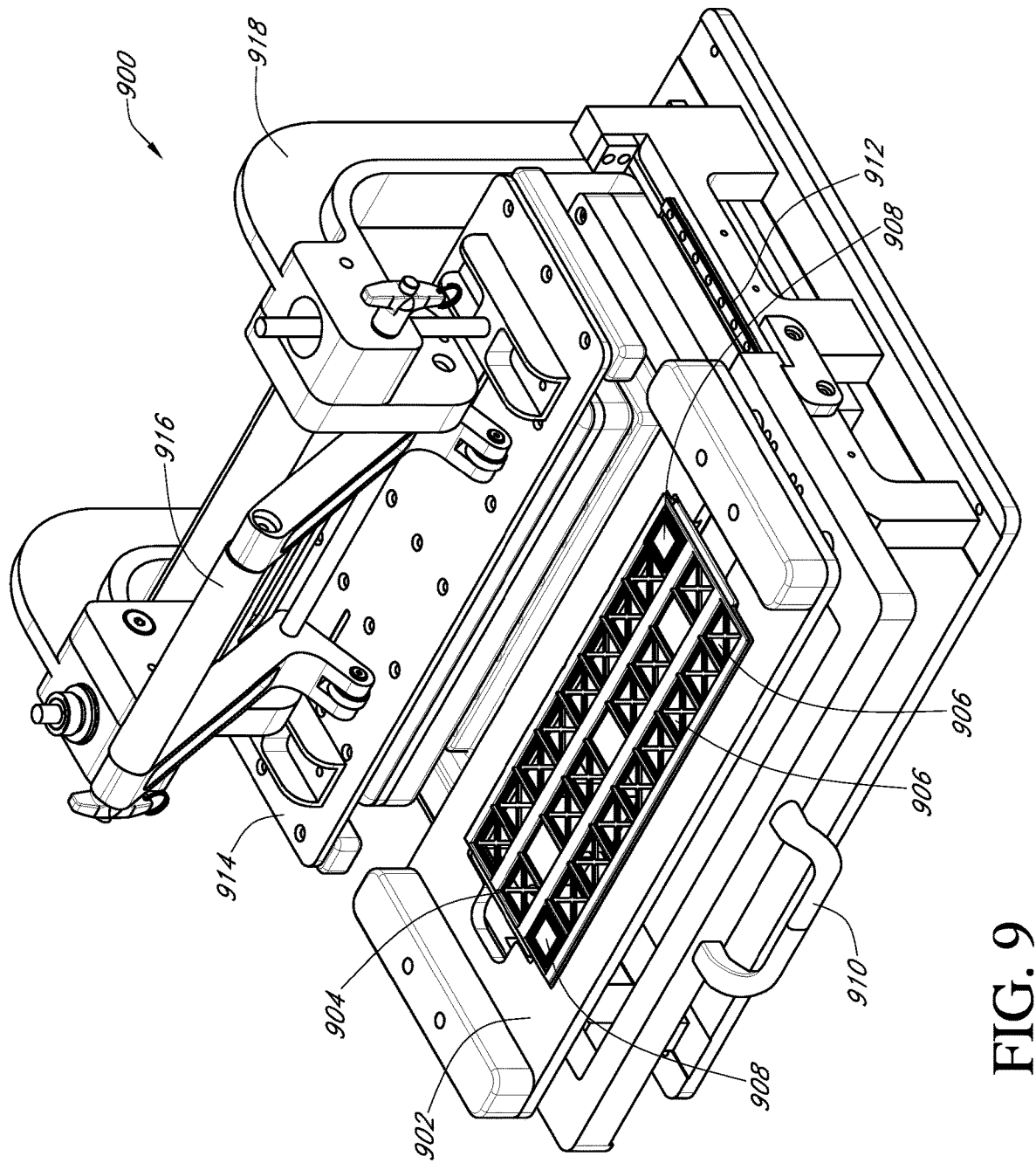
FIG. 9, FIG. 10, FIG. 11, FIG. 12, and FIG. 13 include illustrations of an exemplary preparation manifold of a treatment system.

FIG. 9, FIG. 10, FIG. 11, FIG. 12, and FIG. 13 include illustrations of an exemplary treatment apparatus for treating sensor apparatuses in preparation for packaging and storage. As illustrated in FIG. 9, a treatment apparatus 900 includes a deck 902 configured to secure a tray 904. The tray 904 includes slots 906 to receive sensor apparatuses 908. As illustrated, the sensor apparatuses 908 are applied to have electronic interfaces facing upward and fluidic interfaces to the flow cell facing downward. Alternatively, the sensor apparatuses 908 can be applied to have electronic interfaces facing downward and fluidic interfaces to the flow cell facing downward.

Figure 10:
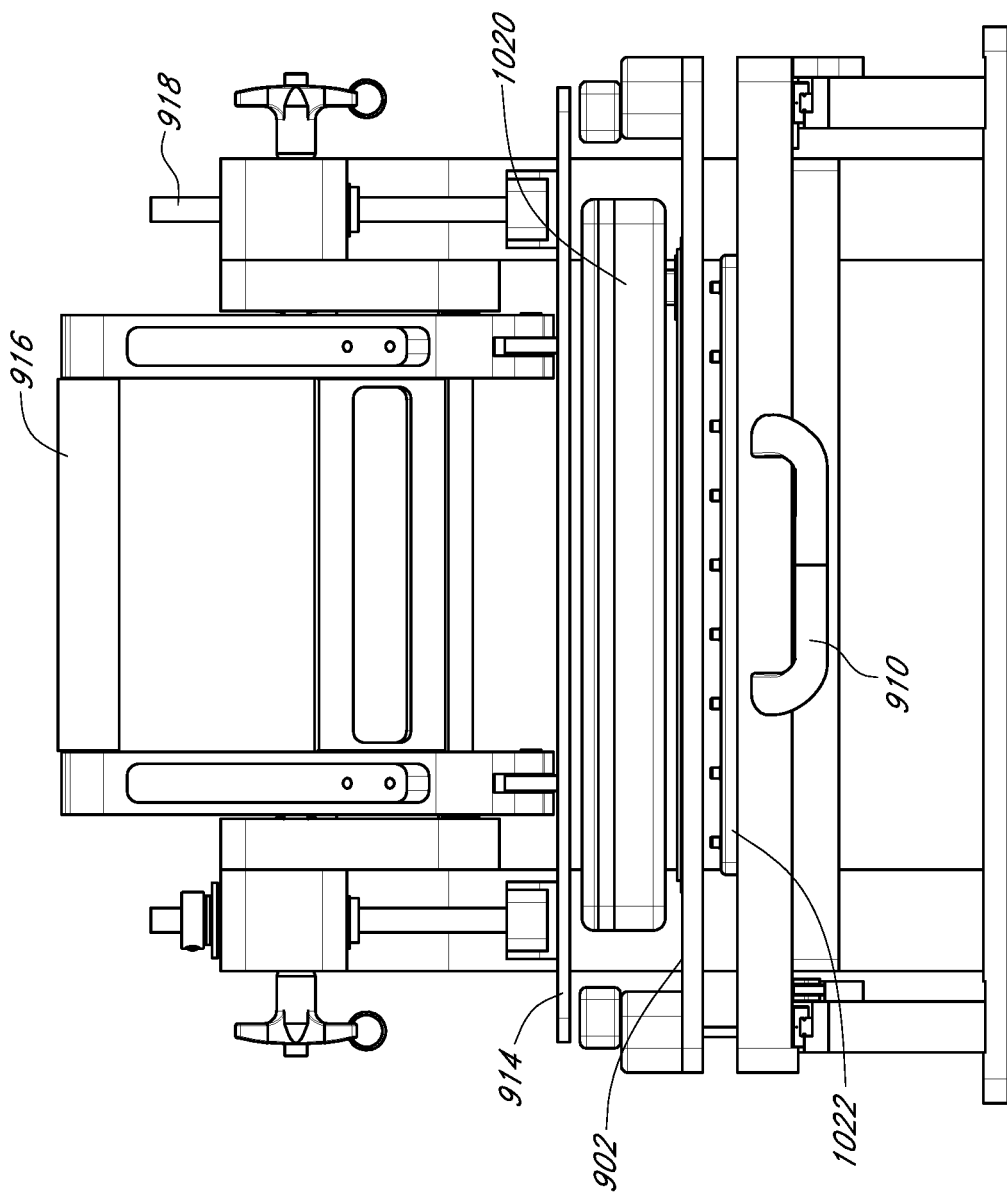
Figure 11:
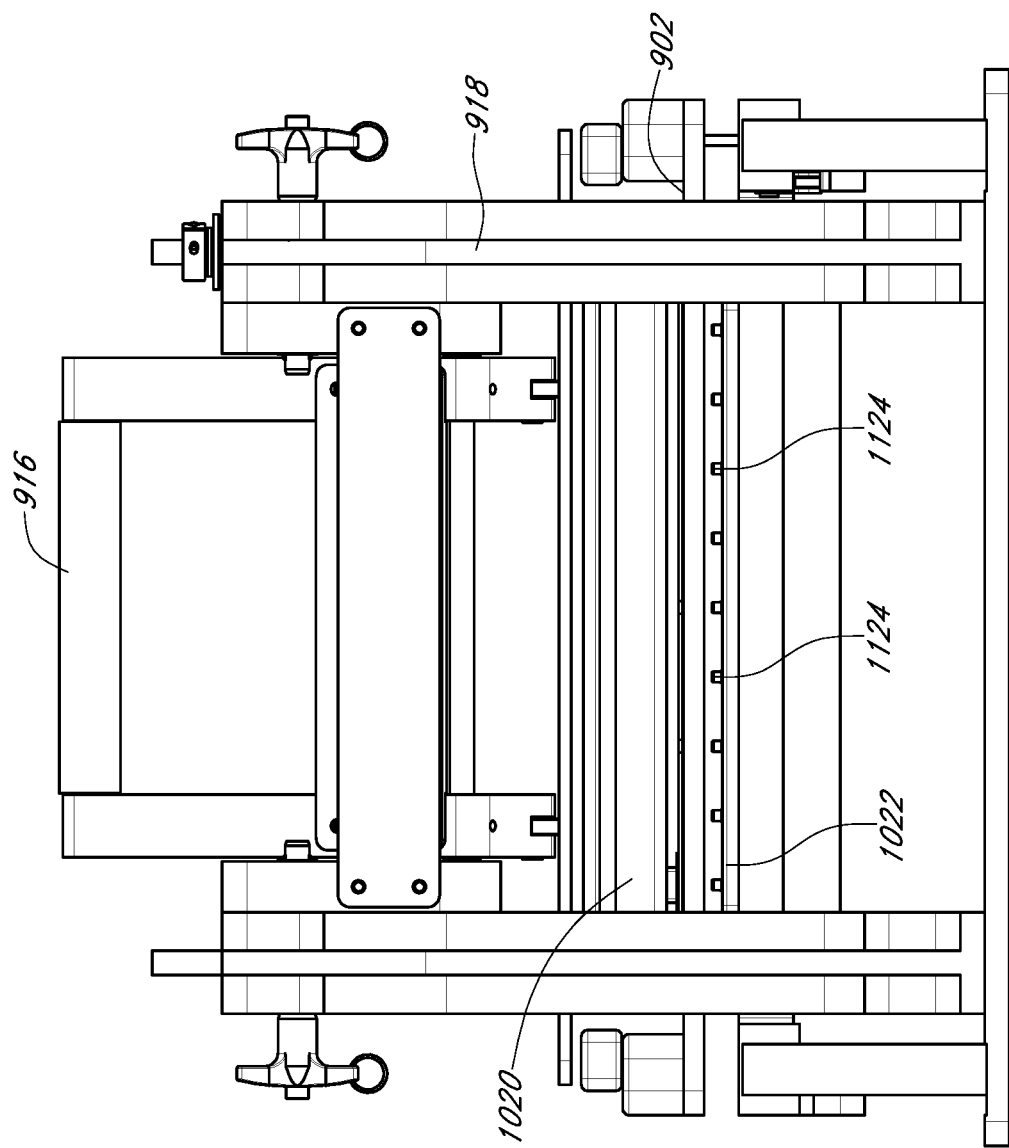
Figure 12:
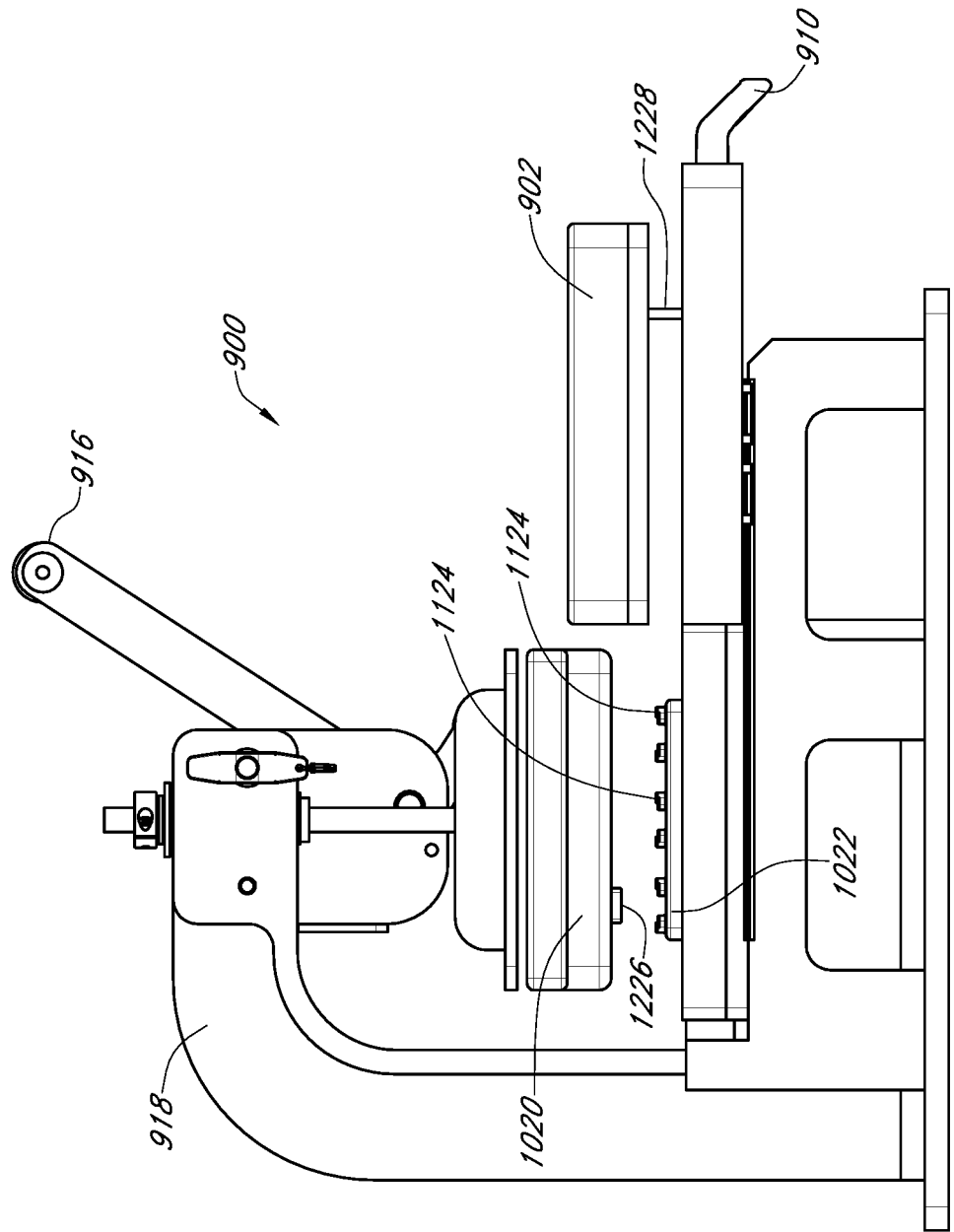
Figure 13:
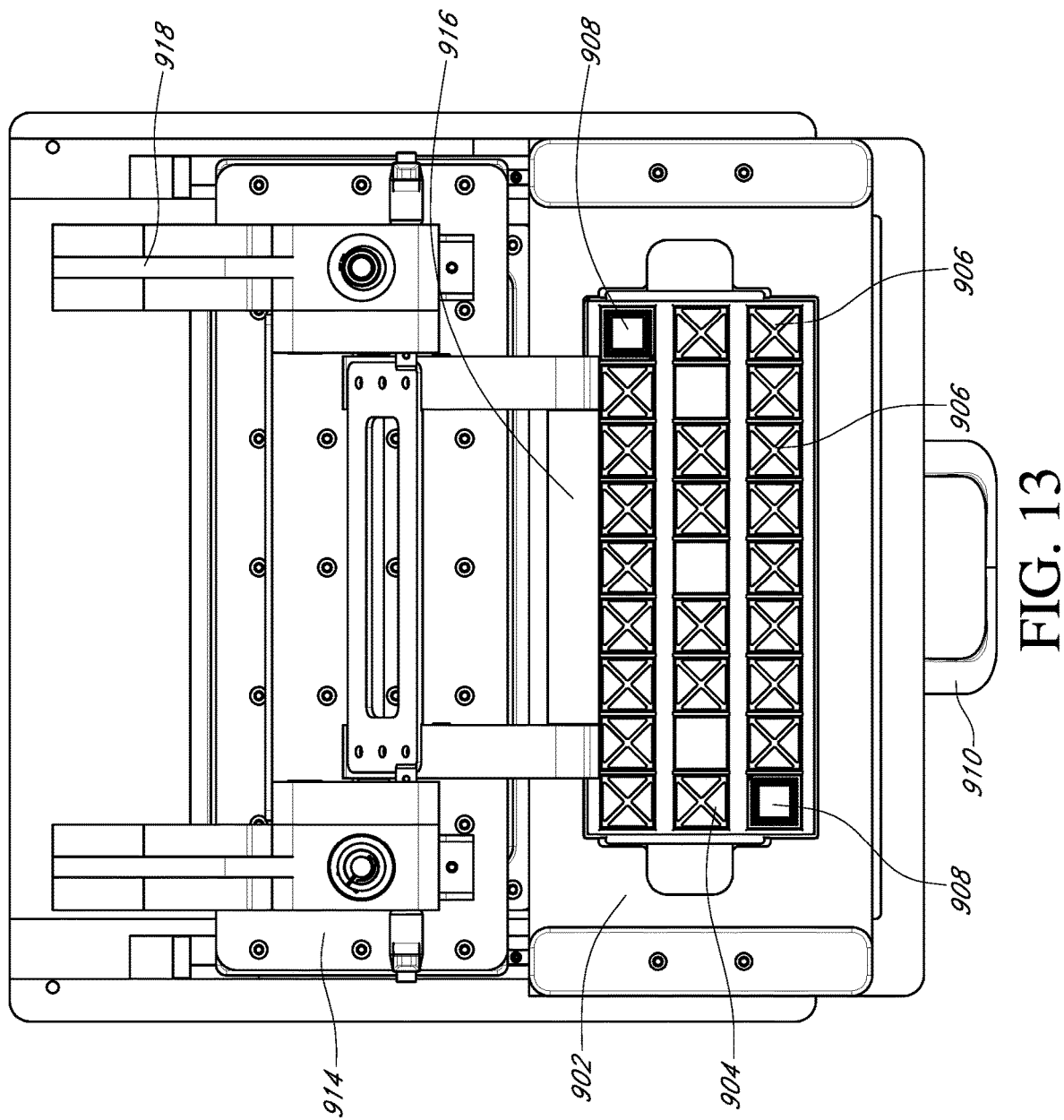

Using a handle 910, the deck 902 can be guided along the rails 912 under the clamp 914. When positioned under the clamp 914, the deck 902 aligns the sensor devices and, in particular, the fluid access to the flow cells of the sensor apparatuses with a fluidics manifold 1022 and ports 1124, as illustrated in FIG. 10 and FIG. 11.

The clamp 914 is supported by supports 918. A handle 916 can motivate the clamp 914 downward, pushing the deck 902 down to engage the fluid manifold 1022. An engagement structure 1020 can include one or more resilient structures 1226 (illustrated in FIG. 12) to engage sensor apparatuses and motivate them against the fluid ports 1124.

As the handle 916 is lowered, the structure 1020 engages the platform 902 and drives the deck 902 and the tray 904 of sensor apparatuses 908 down. The platform 902 is driven along an axle 1228 until the fluid ports of the sensor apparatuses 908 engaged the fluid ports 1124 of the fluid manifold 1022. When the handle 916 driven upward, the platform 902 is driven up along axle 1228, disengaging the sensor apparatuses 908 from the fluid ports 1124. The deck 902 and the sensor apparatuses 908 can be pulled out from under the clamp 914 using the handle 910.

Figure 14:
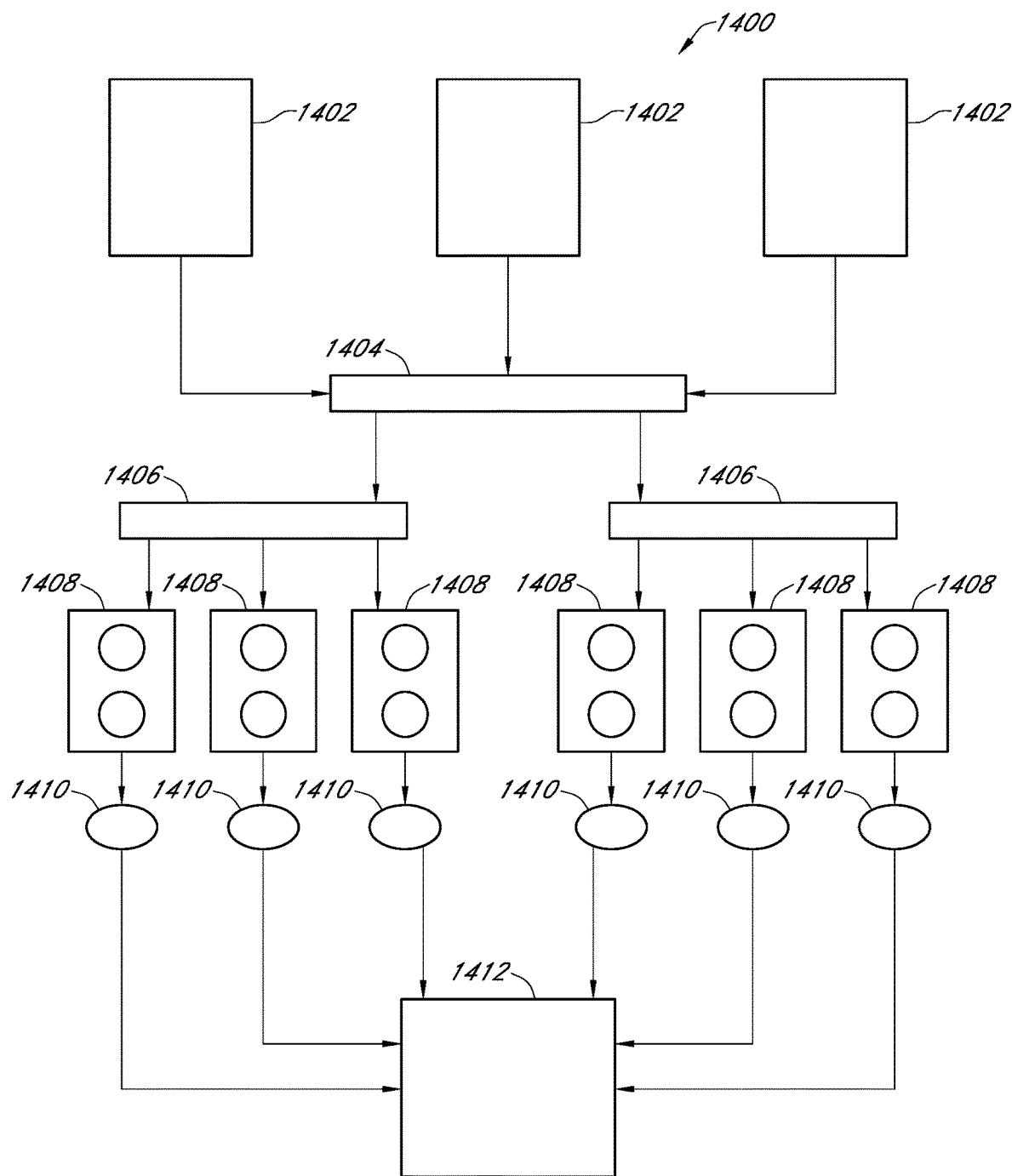
FIG. 14 includes an illustration of an exemplary treatment system.

In a particular example, the manifold 900 forms part of an apparatus to fluidicly engage the fluid ports of sensor apparatuses and apply one or more reagent solutions through flow cells of the sensor apparatuses, including a saccharide solution. For example, as illustrated in FIG. 14, a treatment system 1400 includes reagent containers 1402 connected to a fluid manifold 1404. The fluid manifold 1404 is fluidicly connected to submanifolds 1406 that can each, through the use of the treatment apparatus 900 apply fluid through flow cells of sensor apparatuses 1408. In a particular example, fluid can be driven or drawn from the reagent containers 1402 by pressurizing the containers or through the use of pumps drawing fluid from the containers 1402. The manifold 1404 can selectively flow reagents from the reagent containers 1402 to the submanifolds 1406. The fluid can then flow through the manifold 1404 and the submanifold 1406 through the flow cells of sensor apparatuses 1408 based on the control of the downstream valves 1410. When one of the valves 1410 is open, the fluid can flow through the flow cells of sensor apparatuses 1408 and into the waste container 1412.

In an example, each of the valves 1410 can be open simultaneously allowing continuous flow through the system. Alternatively, sensor apparatuses can be treated individually by selectively flowing a reagent through the manifold 1404 and submanifolds 1406 and selectively through one or more of the sensor apparatuses 1408 based on the position of the valves 1410 downstream of the sensor apparatuses 1408.

For example, the system can include wash solution, acid or base cleaning treatment solutions, and a saccharide solution as described above. For example, awash solution can be applied over one or more sensor apparatuses 1408. The sensor apparatuses can include beads in wells or can be free of beads. A sensor apparatus can be treated using an acid or base treatment solution. In an example, the pretreatment of the sensor apparatuses can influence concentrations of surface hydroxyl groups, influencing signal associated with pH measurement. The surface can be stabilized by applying the saccharide solution through the flow cell the sensor apparatuses and leaving a saccharide coating over the sensor electrodes of the sensor devices and optionally, over a bead. The sensor apparatuses 1408 can be removed from the treatment apparatus, dried, and packaged, ready for transportation and storage.

As described above, surface stabilized biosensors can be washed and used to detect biomolecular targets or associated byproducts. In particular, the biosensors, e.g., the sensor apparatuses, can be washed as described above and applied to a detection system, such as a sequencing system.

In an example, beads or particles to which biomolecules can be or are attached can be applied to the biosensors for determining characteristics of the biomolecules. The beads can be applied following washing the saccharide coating or prior to treatment with the saccharide solution. In particular, the biosensors can be used for sequencing nucleic acid or protein target sequences conjugated to the amplified beads or particles. For example, sequencing can include label-free DNA sequencing, and in particular, pH-based DNA sequencing. Beads or particles including DNA templates and having a primer and polymerase operably bound are loaded into reaction chambers (such as microwells of the sensor apparatus), after which repeated cycles of deoxynucleoside triphosphate (dNTP) addition and washing are carried out. Alternatively, a bead can be present prior to washing, and target nucleic acids can be applied to the bead. Such templates are typically attached as clonal populations to the bead or particle, and such clonal populations are loaded into reaction chambers. In each addition step of the cycle, the polymerase extends the primer by incorporating added dNTP when the next base in the template is the complement of the added dNTP. When there is one complementary base, there is one incorporation, when two, there are two incorporations, when three, there are three incorporations, and so on. With each such incorporation a hydrogen ion is released, and collectively a population of templates releases hydrogen ions causing very slight changes the local pH of the reaction chamber which is detected by an electronic sensor.

Figure 15:
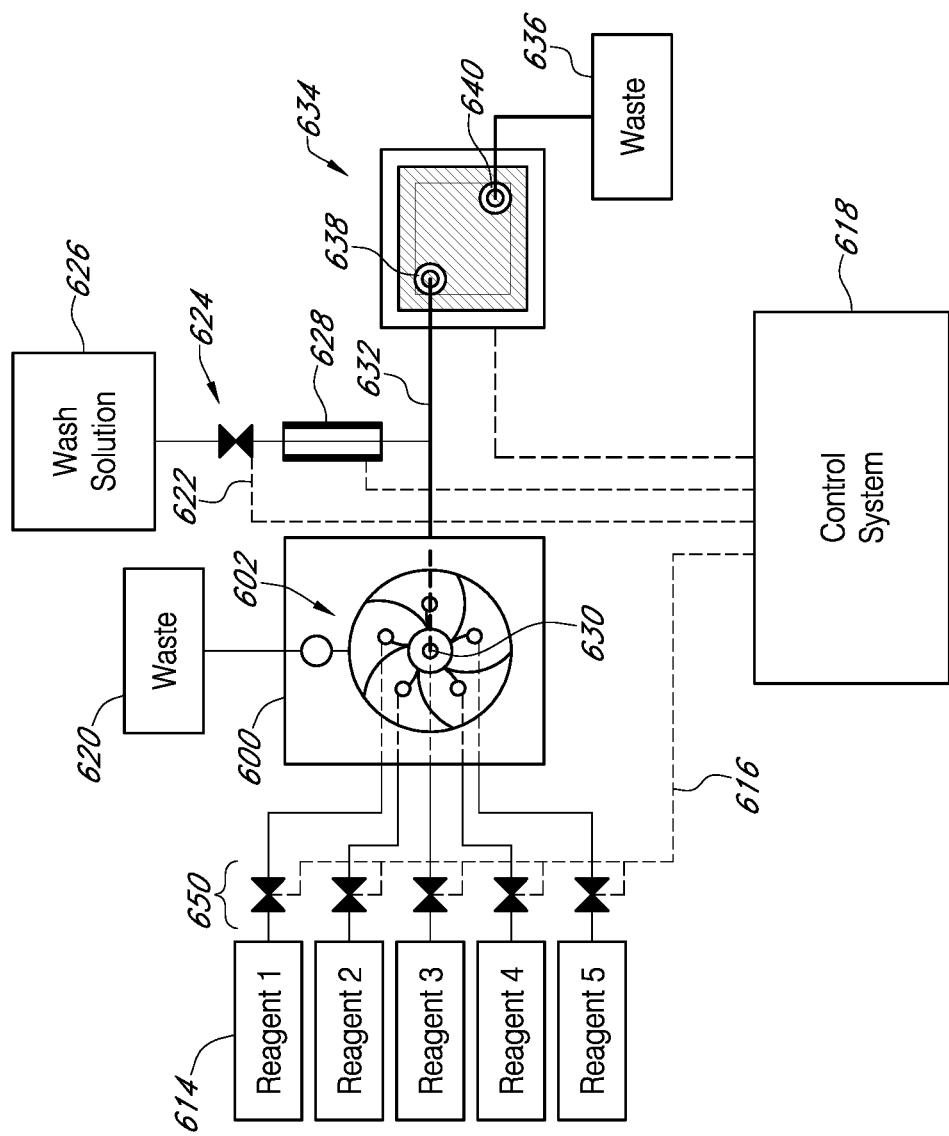
FIG. 15 includes an illustration of an exemplary sensing system.

FIG. 15 diagrammatically illustrates an apparatus for carrying out pH-based nucleic acid sequencing. Each electronic sensor of the sensor apparatus generates an output signal that depends on the value of a reference voltage. In FIG. 15, a housing 600 containing a fluidics circuit 602 is connected by inlets to reagent reservoirs 614, to a waste reservoir 620 and to a flow cell 634 by a passage 632 that connects a fluidics node 630 to an inlet 638 of the flow cell 634. Reagents from the reservoirs 614 can be driven to the fluidic circuit 602 by a variety of methods including pressure, pumps, such as syringe pumps, gravity feed, and the like, and are selected by control of valves 650. A control system 618 includes controllers for valves 650 that generate signals for opening and closing via electrical connection 616. The control system 618 also includes controllers for other components of the system, such as wash solution valve 624 connected thereto by control line 622, and a reference electrode 628. The control system 618 can also include control and data acquisition functions for the flow cell 634. In one mode of operation, the fluidic circuit 602 delivers a sequence of selected reagents (1, 2, 3, 4, or 5) to the flow cell 634 under programmed control of the control system 618, such that in between selected reagent flows, the fluidics circuit 602 is primed and washed, and the flow cell 634 is washed. Fluids entering the flow cell 634 exit through an outlet 640 and are deposited in a waste container 636. Throughout such an operation, the reactions or measurements taking place in the flow cell 634 have a stable reference voltage because the reference electrode 628 has a continuous, i.e. uninterrupted, electrolyte pathway with the flow cell 634, but is in physical contact with only the wash solution.

EXAMPLES

Example 1 pH-based sequencing apparatuses (Ion Torrent™ Proton I) are treated with different solutions including a saccharide or polymer.

The apparatuses are prepared by flowing a series of wash solutions through the flow cells of the apparatuses. A solution including 5 wt % dodecyl benzene sulfonic acid (DBSA) in undecane is flowed through the flow cell for 1 minute. Isopropyl alcohol is flowed through the flow cell to remove the DBSA in undecane. Water is applied through the flow cell followed by a 10 mM NaOH solution for 2:45 min. Water is applied through the flow cell followed by isopropyl alcohol (IPA) and subsequently nitrogen gas.

Following drying under nitrogen, an aqueous solution including 10 wt % or 20 wt % of a selected saccharide or polymer is applied through the flow cell. Controls are not treated. The saccharides are selected from sucrose, galactose, and trehalose. The polymer is selected from a polyethylene glycol polymer (PEG 200 or PEG 1000), polypropylene glycol, an ethylene oxide/propylene oxide block copolymer (Pluronic P65), and a polyol (Pluronic F127). Following application of the solution, the flow cell is flushed with nitrogen. The apparatuses' surfaces are observed for uniformity of coating. The apparatuses are further test for initial bead loading uniformity and for bead loading uniformity after aging (heating at 70° C. for 7 days). Bead loading is performed on an Ion Torrent™ Ion Chef™ using Ion Torrent™ kits incorporating the above chip apparatus.

Those apparatuses treated with sucrose, galactose, and trehalose demonstrate desirable uniformity and both initial and aged bead loading, providing improvement over the control. The polyol polymer demonstrates similar improvement relative to the controls. The ethylene oxide/propylene oxide copolymer solution provides similar to slightly better bead loading relative to the control. The PEG and propylene glycol polymers provide less desirable bead loading than the control.

Example 2 pH-based sequencing apparatuses (ION Torrent Proton I) are treated with saccharide solutions incorporating different surfactants.

The apparatuses are prepared by flowing a series of wash solutions through the flow cells of the apparatuses. A solution including 5 wt % dodecyl benzene sulfonic acid (DBSA) in undecane is flowed through the flow cell for 1 minute. Isopropyl alcohol is flowed through the flow cell to remove the DBSA in undecane. Water is applied through the flow cell followed by a 10 mM NaOH solution for 2:45 min. Water is applied through the flow cell followed by isopropyl alcohol (IPA) and subsequently nitrogen gas.

Following drying under nitrogen, an aqueous saccharide solution including 10 wt % or 20 wt % sucrose and between 0.05 wt % and 0.2 wt % of a select surfactant is applied through the flow cell. The surfactant is selected from 0.05 wt % of a non-ionic fluorosurfactant (Thetawet 8150), 0.02 wt % of a non-ionic surfactant (Triton X-100), 0.1 wt % of an alkyl polysaccharide surfactant (Multitrope), 0.2 wt % dioctyl sodium sulfosuccinate, or 0.2% of a zwitterionic surfactant (Anzergent 3-12). Following application of the saccharide solution, the flow cell is flushed with nitrogen. The apparatuses' surfaces are observed for uniformity of coating.

The saccharide solutions including 10 wt % sucrose provided a more uniform coating and less streaking than the saccharide solutions including 20 wt % sucrose. Each of the surfactants had similar effects on uniformity. But, the Triton X-100 surfactant produced beads of sucrose on a lid of the flow cell.

Example 3

To assess the stability of pre-loaded cassettes on Ion Torrent™ 541 chips, the chips (apparatuses) are pre-loaded with polyacrylamide beads, coated using a sucrose solution, and vacuum sealed with desiccant in a foil pouch.

A set of 16 kits including Ion Torrent 541 chips (apparatuses) and associated polyacrylamide beads are loaded by spinning a solution bearing the beads on the apparatuses for 2 minutes, foam scraping, and flushing and vacuuming. The beads are conjugated to oligonucleotides that act to capture target polynucleotides and extend to make complementary copies of the target polynucleotides.

Half of the apparatuses are coated with a sucrose solution including 1431 g H$_2$O, 358 g sucrose, and 3.5 g Anzergent 3-12. Each of the apparatuses is placed in a tray and vacuum sealed in a foil pouch for storage.

Apparatuses are tested at 1 day, 3 days, and 10 days of storage. The apparatuses are washed to remove the sucrose coating and subjected to amplification to yield beads conjugated to polynucleotides, which are sequenced.

Day 1 apparatuses whether sucrose coated or not demonstrate similar sequencing performance characterized by similar loading percentage, key signal, and q20 mean performance. But, Day 3 apparatuses not stored with a sucrose coating demonstrate a significantly reduced sequencing performance, whereas Day 3 apparatuses stored with a sucrose coating maintain sequencing performance. Day 10 apparatuses stored with a sucrose coating also maintain sequencing performance.

In a first aspect, a sensor apparatus includes a substrate, a semiconductor device disposed over the substrate, the semiconductor device having a surface electrode structure, and a saccharide coating formed over the surface electrode structure.

In an example of the first aspect, the sensor apparatus further includes a well structure defined over the semiconductor device and defining a well exposing the surface electrode structure, the saccharide coating formed at least partially within the well.

In an additional example of the first aspect and the above examples, the apparatus further includes a bead disposed in the well, the saccharide coating formed over the bead. In an example, the bead is conjugated to a nucleic acid. In another example, the bead is a hydrogel bead. In a further example, the bead comprises a polymer selected from the group consisting of agarose; polyethylene glycol; polyoxybutylene; diethylacrylamide; polyoxyethylene; polyacrylamide; polyoxypropylene; N,N-polydimethylacrylamide; poly(N-isopropylacrylamide); polyvinylpyrrolidone; poly-N-hydroxyacrylamide; and any combination thereof. In a particular example, the polymer is polyacrylamide.

In another example of the first aspect and the above examples, the sensor apparatus further includes a flow cell lid disposed over the substrate and defining a flow cell between the substrate and the flow cell lid. The surface electrode structure is accessible through the flow cell.

In a further example of the first aspect and the above examples, the semiconductor device includes a field effect transistor having a gate electrode structure. The surface electrode structure forms at least part of the gate electrode structure.

In an additional example of the first aspect and the above examples, the surface electrode structure includes a conductive structure and a sensor layer disposed over the conductive structure. For example, the sensor layer includes a ceramic layer.

In another example of the first aspect and the above examples, the surface electrode structure includes a floating gate structure.

In a further example of the first aspect and the above examples, the saccharide coating includes a monosaccharide, a disaccharide, a polysaccharide, a derivation thereof, or a combination thereof. For example, the monosaccharide can include glucose, fructose, galactose, or a combination thereof. In an additional example, the disaccharide includes sucrose, trehalose, maltose, or lactose. For example, the disaccharide includes sucrose. In another example, the disaccharide includes trehalose. In a further example, the saccharide includes hyaluronan.

In a second aspect, a sensor apparatus includes a semiconductor substrate, semiconductor devices formed on the semiconductor substrate, a well structure formed over the semiconductor devices and defining a well, wherein the semiconductor devices include a field effect transistor having a gate structure responsive to a condition within the well, and a saccharide coating disposed within the well and over the gate structure.

In an example of the second aspect, the sensor apparatus further includes a flow cell lid disposed over the semiconductor substrate and the well structure and defining a flow cell between the substrate and the flow cell lid, the well exposed to the flow cell.

In another example of the second aspect and the above examples, the apparatus further includes a bead is disposed in the well, the saccharide coating disposed over the bead. In an example, the bead is conjugated to a nucleic acid. In another example, the bead is a hydrogel bead. In an further example, the bead comprises a polymer selected from the group consisting of agarose; polyethylene glycol; polyoxybutylene; diethylacrylamide; polyoxyethylene; polyacrylamide; polyoxypropylene; N,N-polydimethylacrylamide; poly(N-isopropylacrylamide); polyvinylpyrrolidone; poly-N-hydroxyacrylamide; and any combination thereof. In a particular example, the polymer is polyacrylamide.

In another example of the second aspect and the above examples, the gate structure includes a conductive structure and a sensor layer disposed over the conductive structure. For example, the sensor layer includes a ceramic layer.

In a further example of the second aspect and the above examples, the gate structure includes a floating gate structure.

In an additional example of the second aspect and the above examples, the saccharide coating includes a monosaccharide, a disaccharide, a polysaccharide, a derivation thereof, or a combination thereof. For example, the monosaccharide includes glucose, fructose, galactose, or a combination thereof. In another example, the disaccharide includes sucrose, trehalose, maltose, or lactose. For example, the disaccharide includes sucrose. In a further example, the disaccharide includes trehalose. In an additional example, the saccharide includes hyaluronan.

In a third aspect, a method of sequencing includes flowing a wash solution over a sensor apparatus. The sensor apparatus includes a substrate, a semiconductor device disposed over the substrate, the semiconductor device having a surface electrode structure, and a saccharide coating formed over the surface electrode structure. The wash solution removes the saccharide coating. The method further includes applying nucleic acid targets to the sensor apparatus, applying the sensor apparatus to a sequencing system, and sequencing the nucleic acid targets using the sequencing system.

In an example of the third aspect, the saccharide coating includes a monosaccharide, a disaccharide, a polysaccharide, a derivation thereof, or a combination thereof. For example, the monosaccharide includes glucose, fructose, galactose, or a combination thereof. In another example, the disaccharide includes sucrose, trehalose, maltose, or lactose. In an example, the disaccharide includes sucrose. In another example, the disaccharide includes trehalose. In a further example, the saccharide includes hyaluronan.

In an additional example of the third aspect and the above examples, the apparatus further includes a well structure defining a well over the surface electrode structure, and the apparatus further includes a bead disposed in the well. Applying nucleic acid targets to the sensor apparatus includes contacting the nucleic acid targets with the bead. In an example, the bead includes an oligonucleotide complementary to a portion of the nucleic acid target, and the method further includes amplifying the nucleic acid target to form copies of the nucleic acid target on the bead. For example, the bead is a hydrogel bead. In an example, the bead comprises a polymer selected from the group consisting of agarose; polyethylene glycol; polyoxybutylene; diethylacrylamide; polyoxyethylene; polyacrylamide; polyoxypropylene; N,N-polydimethylacrylamide; poly(N-isopropylacrylamide); polyvinylpyrrolidone; poly-N-hydroxyacrylamide; and any combination thereof. In a particular example, the polymer is polyacrylamide.

In a fourth aspect, a method of preparing a sensor apparatus includes applying a cleaning solution through a flow cell lid over a semiconductor substrate defining a flow cell, the semiconductor substrate including a plurality of field effect transistors each including a gate structure exposed to the flow cell, applying a saccharide solution through the flow cell, the solution including a saccharide, and removing the saccharide solution from the flow cell, a layer of the saccharide remaining over the gate structures.

In an example of the fourth aspect, applying the wash solution includes flowing a basic solution through the flow cell prior to applying the solution including the saccharide.

In an additional example of the fourth aspect and the above examples, a well structure defines a well over the gate structure, and the method further includes applying a bead into the well prior to applying the saccharide solution. In an example, the bead is conjugated to a nucleic acid. In another example, the bead is a hydrogel bead. In a further example, the bead comprises a polymer selected from the group consisting of agarose; polyethylene glycol; polyoxybutylene; diethylacrylamide; polyoxyethylene; polyacrylamide; polyoxypropylene; N,N-polydimethylacrylamide; poly(N-isopropylacrylamide); polyvinylpyrrolidone; poly-N-hydroxyacrylamide; and any combination thereof. For example, the polymer is polyacrylamide.

In another example of the fourth aspect and the above examples, applying the wash solution includes flowing a non-aqueous surfactant solution through the flow cell prior to applying the solution including the saccharide. For example, the non-aqueous surfactant solution includes a sulfonic acid surfactant in a non-aqueous solvent.

In a further example of the fourth aspect and the above examples, the saccharide includes a monosaccharide, a disaccharide, a polysaccharide, a derivation thereof, or a combination thereof. For example, the monosaccharide includes glucose, fructose, galactose, or a combination thereof. In an additional example, the disaccharide includes sucrose, trehalose, maltose, or lactose. For example, the disaccharide includes sucrose. In another example, the disaccharide includes trehalose. In another example, the saccharide includes hyaluronic acid.

In an additional example of the fourth aspect and the above examples, the saccharide solution includes the saccharide in a range of 5 wt % to 30 wt %.

In another example of the fourth aspect and the above examples, the saccharide solution includes a surfactant in a range of 0.01 wt % to 10.0 wt %. For example, the surfactant can include a zwitterionic surfactant. In another example, the surfactant includes a non-ionic surfactant.

In a fifth aspect, a method of preparing a sensor apparatus includes applying a flow cell lid over a semiconductor substrate to define a flow cell, the semiconductor substrate including a plurality of field effect transistors each including a gate structure exposed to the flow cell, applying a solution through the flow cell, the solution including a saccharide, and removing the solution from the flow cell, a layer of the saccharide remaining over the gate structures.

In an example of the fifth aspect, the method further includes flowing a basic solution through the flow cell prior to applying the solution including the saccharide.

In another example of the fifth aspect and the above examples, a well structure defines a well over the gate structure, and the method further includes applying a bead into the well prior to applying the saccharide solution. For example, the bead is conjugated to a nucleic acid. In an example, the bead is a hydrogel bead. In another example, the bead includes a polymer selected from the group consisting of agarose; polyethylene glycol; polyoxybutylene; diethylacrylamide; polyoxyethylene; polyacrylamide; polyoxypropylene; N,N-polydimethylacrylamide; poly(N-isopropylacrylamide); polyvinylpyrrolidone; poly-N-hydroxyacrylamide; and any combination thereof. In a particular example, the polymer is polyacrylamide.

In another example of the fifth aspect and the above examples, the method further includes flowing a non-aqueous surfactant solution through the flow cell prior to applying the solution including the saccharide. For example, the non-aqueous surfactant solution includes a sulfonic acid surfactant in a non-aqueous solvent.

In a further example of the fifth aspect and the above examples, the saccharide coating includes a monosaccharide, a disaccharide, a polysaccharide, a derivation thereof, or a combination thereof. For example, the monosaccharide includes glucose, fructose, galactose, or a combination thereof. In an example, the disaccharide includes sucrose, trehalose, maltose, or lactose. For example, the disaccharide includes sucrose. In another example, the disaccharide includes trehalose. In an additional example, the saccharide includes hyaluronic acid.

In an additional example of the fifth aspect and the above examples, the saccharide solution includes the saccharide in a range of 5 wt % to 30 wt %.

In another example of the fifth aspect and the above examples, the saccharide solution includes a surfactant in a range of 0.01 wt % to 10.0 wt %. For example, the surfactant includes a zwitterionic surfactant. In another example, the surfactant includes a non-ionic surfactant.

In an sixth aspect, a treatment system includes a plurality of reagent vessels, a manifold in fluidic communication with the plurality of reagent vessels, and a treatment apparatus including a slidable deck to receive sensor apparatuses, a clamp having resilient apparatus guides, and an access manifold in fluidic communication with the manifold and including ports to fluidicly connect with flow cells of the sensor apparatuses, when the slidable deck is positioned under the clamp, the clamp movable to motivate the slidable deck downward to engage the access manifold.

In an example of the sixth aspect, the slidable deck is to receive the sensor apparatuses with flow cell ports of the sensor apparatuses facing down, the resilient apparatus guides to engage a side of the sensor apparatuses opposite the flow cell ports.

Such methods and devices formed using such methods provide technical advantages relating to improved measurement quality. It has been discovered that signal quality can variably degrade, depending upon factors associated with transportation and storage. Reducing the variability in signal quality provides for a more uniform signal measurement that can lead to more accurate sequence detection.

In particular, pH-based sensor devices, such as those used in pH-based sequencing, are sensitive to factors associated with transportation and storage. It is believed that surface groups, such as surface hydroxyl groups, influence signal quality and that the concentration of such surface groups can be influenced by the factors associated with packaging, transportation, and storage, such as temperature and humidity. The proposed system and methods provides for less variability is signal quality.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed:

1. A treatment system comprising:
a plurality of reagent vessels;
a manifold in fluidic communication with the plurality of reagent vessels; and
a treatment apparatus including a slidable deck to receive sensor apparatuses, a clamp having resilient apparatus guides, and an access manifold in fluidic communication with the manifold and including ports to fluidically connect with flow cells of the sensor apparatuses, when the slidable deck is positioned under the clamp, the clamp movable to motivate the slidable deck downward to engage the access manifold.

* * * * *

UNITED STATES PATENT AND TRADEMARK OFFICE
CERTIFICATE OF CORRECTION

PATENT NO. : 12,139,758 B2  
APPLICATION NO. : 18/407234  
DATED : November 12, 2024  
INVENTOR(S) : Philip Waggoner et al.

Page 1 of 1

It is certified that error appears in the above-identified patent and that said Letters Patent is hereby corrected as shown below:

On the Title Page

In Column 1, under Related U.S. Application Data, Line 1, delete "(60)" and insert -- (63) --, therefor.

Signed and Sealed this
Twenty-eighth Day of January, 2025

Coke Morgan Stewart
*Acting Director of the United States Patent and Trademark Office*